United States Patent
Okumura et al.

(10) Patent No.: US 10,529,548 B2
(45) Date of Patent: *Jan. 7, 2020

(54) LIQUID SAMPLE INTRODUCTION SYSTEM FOR ION SOURCE

(71) Applicant: SHIMADZU CORPORATION, Kyoto-shi, Kyoto (JP)

(72) Inventors: Daisuke Okumura, Kyoto (JP); Yusuke Sakagoshi, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/764,129

(22) PCT Filed: Sep. 29, 2015

(86) PCT No.: PCT/JP2015/077415
§ 371 (c)(1),
(2) Date: Sep. 27, 2018

(87) PCT Pub. No.: WO2017/056173
PCT Pub. Date: Apr. 6, 2017

(65) Prior Publication Data
US 2019/0013189 A1 Jan. 10, 2019

(51) Int. Cl.
*H01J 49/04* (2006.01)
*G01N 27/62* (2006.01)
(Continued)

(52) U.S. Cl.
CPC ............ *H01J 49/045* (2013.01); *G01N 27/62* (2013.01); *G01N 30/724* (2013.01); *H01J 49/40* (2013.01)

(58) Field of Classification Search
CPC ...... H01J 49/045; H01J 49/04; H01J 49/0404; H01J 49/0445; H01J 49/107; G01N 27/62;
(Continued)

(56) References Cited

U.S. PATENT DOCUMENTS 5,703,360 A 12/1997 Fischer et al.
6,207,954 B1 3/2001 Andrien, Jr. et al.
(Continued)

FOREIGN PATENT DOCUMENTS

JP 2008-014788 A 1/2008
JP 2009-031113 A 2/2009
(Continued)

OTHER PUBLICATIONS

Written Opinion of PCT/JP2015/077469 dated Dec. 8, 2015 [PCT/ISA/237].
(Continued)

*Primary Examiner* — Brooke Purinton
(74) *Attorney, Agent, or Firm* — Sughrue Mion, PLLC

(57) ABSTRACT

A liquid sample introduction system for an ion source which ionizes a liquid sample by supplying the liquid sample to an ionization probe 30 in an ion source and making an atomization-promoting gas blow at the liquid sample exiting from the tip of the ionization probe 30, the liquid sample introduction system including: a liquid sample container 70a-70f which is a hermetically closable container for holding a liquid sample; a liquid-supply-gas passage 50 having one end connected to a point in a passage 41 for supplying an atomization-promoting gas to the ion source, and the other end connected to a space above a liquid level in the liquid sample container 70a-70f; and a sample supply passage 60 having one end connected to a space below the liquid level (Continued)

in the liquid sample container 70a-70f and the other end connected to the ionization probe 30.

9 Claims, 3 Drawing Sheets

(51) Int. Cl.
*G01N 30/72* (2006.01)
*H01J 49/40* (2006.01)

(58) Field of Classification Search
CPC .. G01N 30/7233; G01N 30/7266; G01N 1/02; G01N 2030/628
See application file for complete search history.

(56) References Cited

U.S. PATENT DOCUMENTS

| | | | | |
|---|---|---|---|---|
| 7,217,919 | B2* | 5/2007 | Boyle | H01J 49/063 250/281 |
| 2008/0237458 | A1 | 10/2008 | Wang | |
| 2009/0242749 | A1* | 10/2009 | Bajic | H01J 49/04 250/282 |
| 2009/0314057 | A1 | 12/2009 | Hatscher et al. | |
| 2010/0096542 | A1 | 4/2010 | Whitehouse et al. | |
| 2013/0146479 | A1 | 6/2013 | Brouwer et al. | |
| 2014/0284473 | A1* | 9/2014 | Ueda | H01J 49/0445 250/288 |
| 2014/0373605 | A1 | 12/2014 | Nichols et al. | |
| 2015/0102232 | A1 | 4/2015 | Satake et al. | |

FOREIGN PATENT DOCUMENTS

| | | |
|---|---|---|
| JP | 5740525 B2 | 6/2015 |
| WO | 2013132676 A1 | 9/2013 |

OTHER PUBLICATIONS

International Search Report of PCT/JP2015/077469 dated Dec. 8, 2015 [PCT/ISA/210].
Written Opinion of the International Searching Authority of PCT/JP2015/077415 dated Dec. 8, 2015.
International Search Report of PCT/JP2015/077415 dated Dec. 8, 2015.
Non-Final Office Action dated May 21, 2019 issued in related U.S. Appl. No. 15/763,951.
Extended European Search Report dated Jul. 23, 2019 issued by the European Patent Office in counterpart application No. 15905328.9.

* cited by examiner

| Component Name | Retention Time | Mass Range to Be Measured | Liquid Sample Container (Reference Liquid Sample) | Valve Position |
|---|---|---|---|---|
| Component A | 3.0-4.0min. | 10-500 | 70a | a |
| Component B | 5.0-6.0min. | 300-2000 | 70b | b |
| Component C | 8.0-9.5min. | 500-3000 | 70d | d |

LIQUID SAMPLE INTRODUCTION SYSTEM FOR ION SOURCE

CROSS REFERENCE TO RELATED APPLICATIONS

This application is a National Stage of International Application No. PCT/JP2015/077415 filed Sep. 29, 2015.

TECHNICAL FIELD

The present invention relates to a liquid sample introduction system for an ion source used for introducing a liquid sample into an ion source in an ion analyzer, such as a mass spectrometer.

BACKGROUND ART

A mass spectrometer is one type of device for analyzing components contained in a liquid sample. A mass spectrometer includes an ion source for ionizing components in a liquid sample and a mass spectrometry section for separating and detecting the ionized components according to their mass-to-charge ratios. In an ion source for ionizing a liquid sample (e.g. ESI source or APCI source), the ionization of a liquid sample is normally achieved by supplying the liquid sample to an ionization probe and making an atomization-promoting gas (which may also be called a "nebulizer gas" or "drying gas") blow at the liquid sample exiting from the tip of the ionization probe.

For example, a liquid sample introduction system described in Patent Literature 1 is used to introduce a liquid sample into the previously described type of ion source. In this liquid sample introduction system, a liquid-supply gas is sent into the space above the liquid surface in a hermetically closable container holding a liquid sample (liquid sample container) to supply the liquid sample from the liquid sample container to the ionization probe of the ion source by the pressure of the liquid-supply gas.

CITATION LIST

Patent Literature

Patent Literature 1: U.S. Pat. No. 5,703,360 A

SUMMARY OF INVENTION

Technical Problem

The previously described liquid sample introduction system requires the liquid-supply gas for sending a liquid sample in addition to the atomization-promoting gas which is made to blow at the liquid sample in the ion source. The necessity of preparing gas sources for the two kinds of gas inevitably increases the cost of the device.

Although the description thus far has been concerned with a mass spectrometer, a similar problem occurs in an ion mobility spectrometer or other types of devices in which ions are generated from a liquid sample and subjected to analysis.

The problem to be solved by the present invention is to provide a liquid sample introduction system for an ion source with which liquid, samples can be ionized at a low cost.

Solution to Problem

The present invention developed for solving the previously described problem is a liquid sample introduction system for an ion source which ionizes a liquid sample by supplying the liquid sample to an ionization probe in an ion source and making an atomization-promoting gas blow at the liquid sample exiting from the tip of the ionization probe, the liquid sample introduction system including:

a) a liquid sample container which is a hermetically closable container for holding a liquid sample;

b) a liquid-supply-gas passage having one end connected to a point in a passage for supplying an atomization-promoting gas to the ion source, and the other end connected to a space above a liquid level the liquid sample container; and c) a sample supply passage having one end connected to a space below the liquid level in the liquid sample container and the other end connected to the ionization probe.

In the liquid sample introduction system for an ion source according to the present invention, the liquid-supply-gas passage is connected to a point in the passage for supplying atomization-promoting gas to the ion source. A portion of the atomization-promoting gas is thereby introduced into the liquid sample container, and the liquid sample is sent from the liquid sample container to the ionization probe of the ion source by the pressure of the atomization-promoting gas. In other words, the atomization-promoting gas intended for use in the ion source is additionally used as the liquid-supply gas. Accordingly, it is unnecessary to add a supply source of the liquid-supply gas for sending the liquid sample to the ion source, and the ionization of the liquid sample can be achieved at a low cost.

In the liquid sample introduction system for an ion source according to the present invention, the liquid-supply-gas passage is connected to a point in the passage for the atomization-promoting gas, and thus the passage is branched. The atomization-promoting gas is supplied to both of two passages that are branched. If the atomization-promoting gas were supplied for supplying the liquid sample, by using a passage switching valve, the atomization-promoting gas would not be supplied to the ion source while the atomization-promoting gas were supplied to the liquid-supply-gas passage. This would change the pressure and the state of the gas stream inside the ion source (more specifically, the inside of the ionization chamber), causing the types of ions generated from the liquid sample to be changed, as well as the generation efficiency of the ions to fluctuate. In the liquid sample introduction system for an ion source according to the present invention, the atomization-promoting gas can be concurrently supplied to the atomization-promoting gas passage and the liquid-supply-gas passage. Accordingly, the pressure and the state of the gas stream inside the ionization chamber can be stabilized, so that the ions can be generated from the liquid sample under a constant condition.

For the ionization of a liquid sample, a drying gas may additionally be used with the atomization-promoting gas. Such an ion source might allow the drying gas to be used for the supply of the liquid sample. However, this idea is only applicable in an ion source which uses a drying gas. The liquid sample introduction system for an ion source according to the present invention utilizes the atomization-promoting gas, which is commonly used for ionizing a liquid sample by atmospheric pressure ionization regardless of the kind of liquid sample. Therefore, the present system can be used for various kinds of liquid samples and various types of ion sources.

The liquid sample introduction system for an ion source according to the present invention may preferably include a liquid-supply-gas pressure regulator for regulating the pressure of the gas flowing through the liquid-supply-gas passage.

In the aforementioned mode of the liquid sample introduction system for an ion source including the liquid-supply-gas pressure regulator, the pressure of the liquid-supply gas can be regulated independently of the pressure of the atomization-promoting gas supplied to the ion source, so as to change the amount of liquid sample to be supplied to the ion source.

Patent Literature 1 discloses a configuration in which a liquid-supply-gas passage and a sample supply passage are attached to each of plural sample containers each of which contains a liquid sample. Furthermore, a passage-switching valve for switching the connection/block of a passage is provided for each of the plural liquid-supply-gas passages and each of the plural sample supply passages, and thus the plural liquid samples are selectively introduced into the ion source. In this configuration, two passage-switching valves (i.e., the passage-switching valve attached to the liquid-supply-gas passage and the one attached to the sample supply passage) are incorporated in the passage for a single liquid sample. Accordingly, the number of the passage switching valves increases as the types of liquid samples increase, causing the risk of generation of contaminations to increase in those passage-switching valves.

Accordingly, the liquid sample introduction system for an ion source according to the present invention may be configured as follows:

a plurality of the liquid sample containers are provided;

the other end of the liquid-supply-gas passage is branched into a plurality of liquid-supply-gas sub-passages each of which is connected to the space above the liquid level in one of the liquid sample containers; and the one end of the sample-supply passage is branched into a plurality of sample-supply sub-passages each of which is connected to the space below the liquid level in one of the liquid sample containers, and the liquid sample introduction system further includes a passage-switching unit, located at the branching point of the liquid-supply-gas passage, for selectively making one of the plurality of liquid-supply-gas sub-passages be in a communicating state, or a passage-switching unit, located at the branching point of the sample supply passage, for selectively making one of the plurality of sample-supply sub-passages be in a communicating state.

In the previous mode of the liquid sample introduction system for an ion source, it is preferable that the passage-switching unit is located at a branching point of the sample supply passage, for selectively making one of the sample-supply sub-passages be in a communicating state. The use of such a passage-switching unit enables a state in which the pressures of a plurality of the liquid sample containers are simultaneously increased to be maintained. This shortens the dead time upon switching the liquid samples to be supplied to the ionization probe.

For the passage-switching unit, a passage-switching valve can be used, for example. The passage-switching valve has a main port and a plurality of sub-ports to be selectively connected to the main port. In this mode, only one passage-switching unit is used to selectively introduce a plurality of liquid samples into an ion-source liquid supply passage. Therefore, the risk of generation of contaminations at the passage-switching unit can be reduced, in comparison with the liquid sample introduction system disclosed in Patent Literature 1.

Advantageous Effects of the Invention

With the liquid sample introduction system for an ion source according to the present invention, a liquid sample can be introduced into and ionized by an ion source at a low cost.

DESCRIPTION OF EMBODIMENTS

Figure 1:
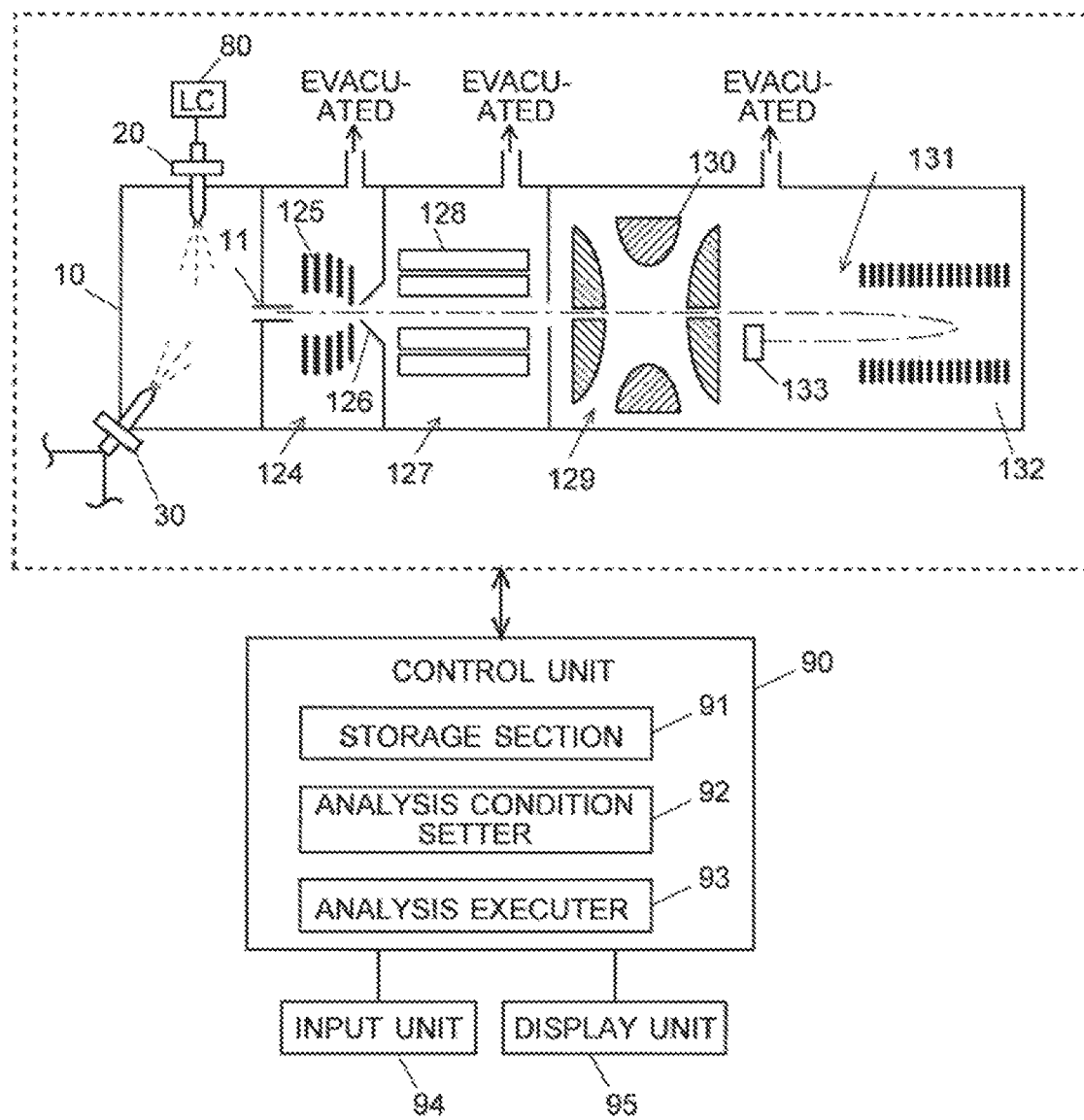
FIG. 1 is a configuration diagram showing the main components of a mass spectrometer including a liquid sample introduction system for an ion source according to the present invention.
Figure 2:
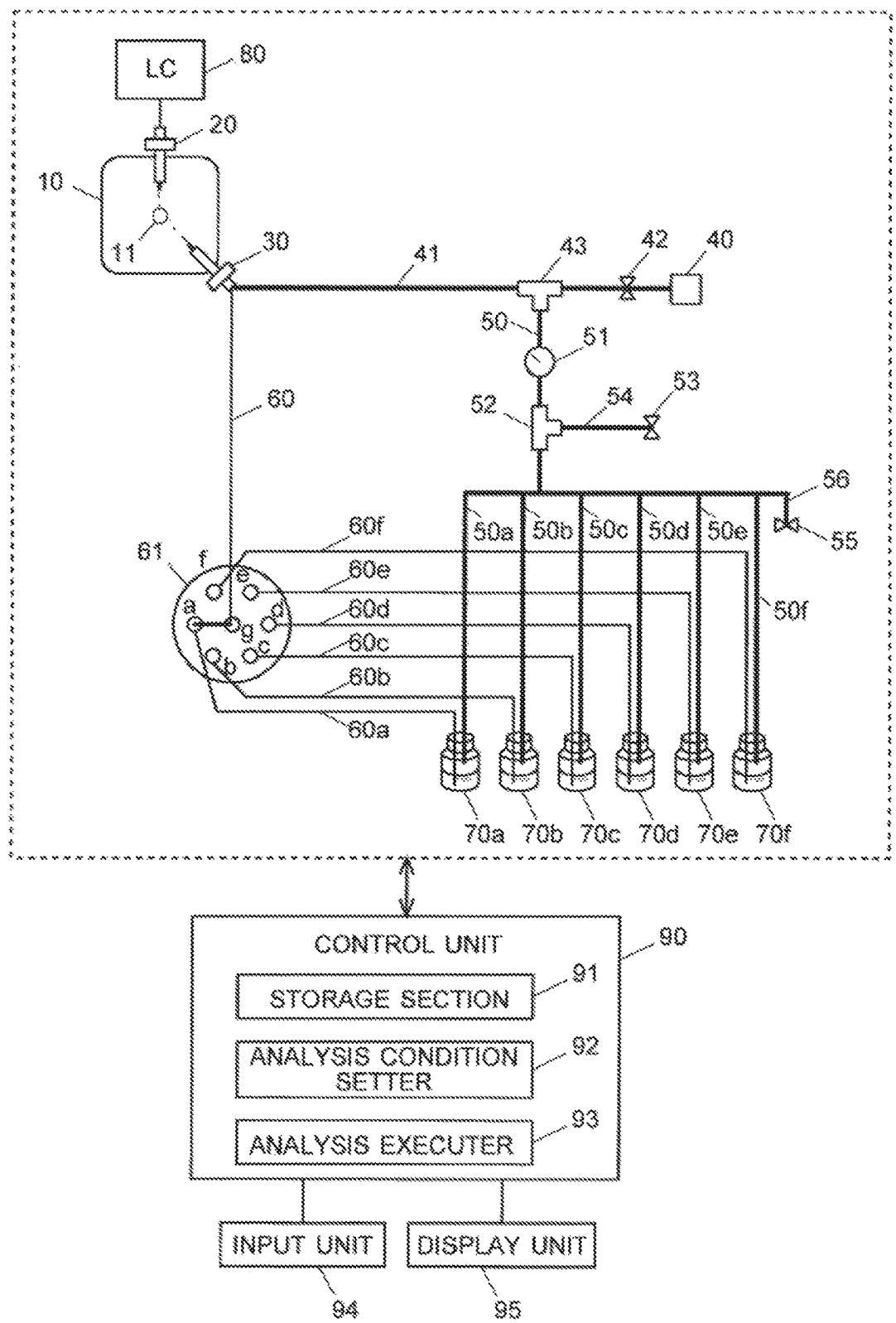
FIG. 2 is a configuration example of the liquid sample introduction system for an ion source according to the present invention.

An embodiment of the liquid sample introduction system for an ion source according to the present invention is hereinafter described with reference to the drawings. The liquid sample introduction system for an ion source according to the present embodiment is used for introducing a reference liquid sample for mass calibration into a time-of-flight mass spectrometer (which may hereinafter be called the "TOF-MS") in a mass spectrometric analysis for various components in a liquid sample to be analyzed (which is hereinafter called the "target liquid sample") which is eluted from a liquid chromatograph 80. Although a TOF-MS is used as the ion analyzer in the present embodiment, a liquid sample introduction system for an ion source having a similar configuration to the present embodiment can also be used in other types of mass spectrometers or ion analyzers (e.g. ion mobility spectrometers).

Each section of the liquid chromatograph 80, liquid sample introduction system for an ion source, and TOF-MS is controlled by a control unit 90. The control unit 90 includes a storage section 91 as well as an analysis condition setter 92 and an analysis executer 93 as its functional blocks. The control unit 90 is actually a computer on which the required software has been installed. An input unit 94 and a display unit 95 are connected to the control unit 90. The analysis condition setter 92 sets analysis conditions based on an input by a user, prepares an analysis execution file, and saves it to the storage section 91. Upon receiving a command issued by the user, the analysis executer 93 conducts an analysis for various components in the target liquid sample by operating each section of the liquid chromatograph 80, liquid sample introduction system for an ion source, and TOF-MS based on the analysis execution file.

The TOF-MS includes an ionization chamber 10 maintained at atmospheric pressure and an analysis chamber 129 maintained in a high vacuum state by being evacuated with a vacuum pump (not shown). First and second intermediate vacuum chambers 124 and 127 having their degrees of vacuum increased in a stepwise manner are located between the ionization chamber 10 and the analysis chamber 129. The ionization chamber 10 communicates with the first intermediate vacuum chamber 124 through a thin desolvation tube 11. The first intermediate vacuum chamber 124 communicates with the second intermediate vacuum chamber 127 through a small orifice bored at the apex of a conical skimmer 126.

The various components in a target liquid sample which have been temporally separated by the column of the liquid chromatograph 80 are turned into electrically charged droplets by an ESI probe 20 and sprayed into the ionization chamber 10. Similarly, a reference liquid sample for mass calibration supplied from a liquid sample introduction system for an ion source (which will be described later) is also transformed into electrically charged droplets by an ESI probe 30 and sprayed into the ionization chamber 10. Those charged droplets collide with gas molecules within the ionization chamber 10, being broken into even finer droplets, which are quickly dried (desolvated) and turned into ions. Due to the pressure difference between the ionization chamber 10 and the first intermediate vacuum chamber 124, those ions are drawn into the desolvation tube 11. Being converged by ion guides 125 and 128, the ions travel through the two intermediate vacuum chambers 124 and 127, to be introduced into a three-dimensional quadrupole ion trap 130 inside the analysis chamber 129.

In the ion trap 130, the ions are temporarily captured by and stored in a quadrupole electric field created by radio-frequency voltages applied from a power source (not shown) to the electrodes. The various ions stored within the ion trap 130 are simultaneously given a specific amount of kinetic energy and thereby ejected from the ion trap 130 into a time-of-flight mass separator (TOF) 131. The TOF 131 includes reflectron electrodes 132, to which DC voltages are respectively applied from a DC power source (not shown). Due to the effect of the DC electric field created by those electrodes, the ions are returned and reach an ion detector 133. Among the ions which have been simultaneously ejected from the ion trap 130, an ion having a smaller mass-to-charge ratio flies at a higher speed. Accordingly, the ions arrive at the ion detector 133 showing time differences depending on their mass-to-charge ratios. The ion detector 133 generates, as a detection signal, an electric current corresponding to the number of ions which have arrived at the detector. The output signals from the ion detector 133 are saved in the storage section 91 of the control unit 90 (which will be described later).

As just described, the liquid sample introduction system for an ion source according to the present embodiment is a system for introducing a reference liquid sample for mass calibration into the ionization chamber 10 of the TOF-MS to ionize the reference liquid sample along with the liquid sample eluted from the column of the liquid chromatograph 80. Each of the six reference liquid samples a-f contains components which produce ions having mass to charge ratios different from one another and is contained in liquid sample containers 70a-70f respectively.

A nebulizer gas passage 41 extending from a nitrogen gas cylinder (atomization gas source) 40 is connected to the ESI probe 30 provided in the ionization chamber 10. In the nebulizer gas passage 41, a valve 42 and a branching unit 43 are provided in the mentioned order from the nitrogen gas cylinder 40. A liquid-supply-gas passage 50 is connected to the branching unit 43. The liquid-supply-gas passage 50 is provided with a regulator 51 and a branching unit 52. A relief passage 54 leading to a relief valve 53 is connected to the branching unit 52.

The liquid-supply-gas passage 50 is branched into six liquid-supply-gas sub-passages 50a-50f. The ends of the liquid-supply-gas sub-passages 50a-50f are respectively led to the spaces above the liquid levels in the containers (liquid sample containers) 70a-70f each of which contains a reference liquid sample. An atmospheric open passage 56 leading to an atmospheric open valve 55 is provided parallel to the liquid-supply-gas sub-passages 50a-50f.

Additionally, a sample supply passage 60 is connected to the ESI probe 30. The other end of the sample supply passage 60 is connected to the main port 61g of a six-position seven-way valve 61. The six-position seven-way valve 61 has six sub-ports 61a-61f. One of the sub-ports 61a-61f can be connected to the main port 61g. One end of each of the sample-supply sub-passages 60a-60f is connected to each of the sub-ports 61a-61f. The other ends of the sample-supply sub-passages 60a-60f are respectively led to the spaces below the liquid levels (i.e. submerged in the liquid) in the liquid sample containers 70a-70f. One end of an atmospheric open passage 62 is connected to the sub-port 61f. The other end of the atmospheric open passage 62 is open to the atmosphere.

An analysis operation in the present embodiment is hereinafter described.

Figures 3, 4:
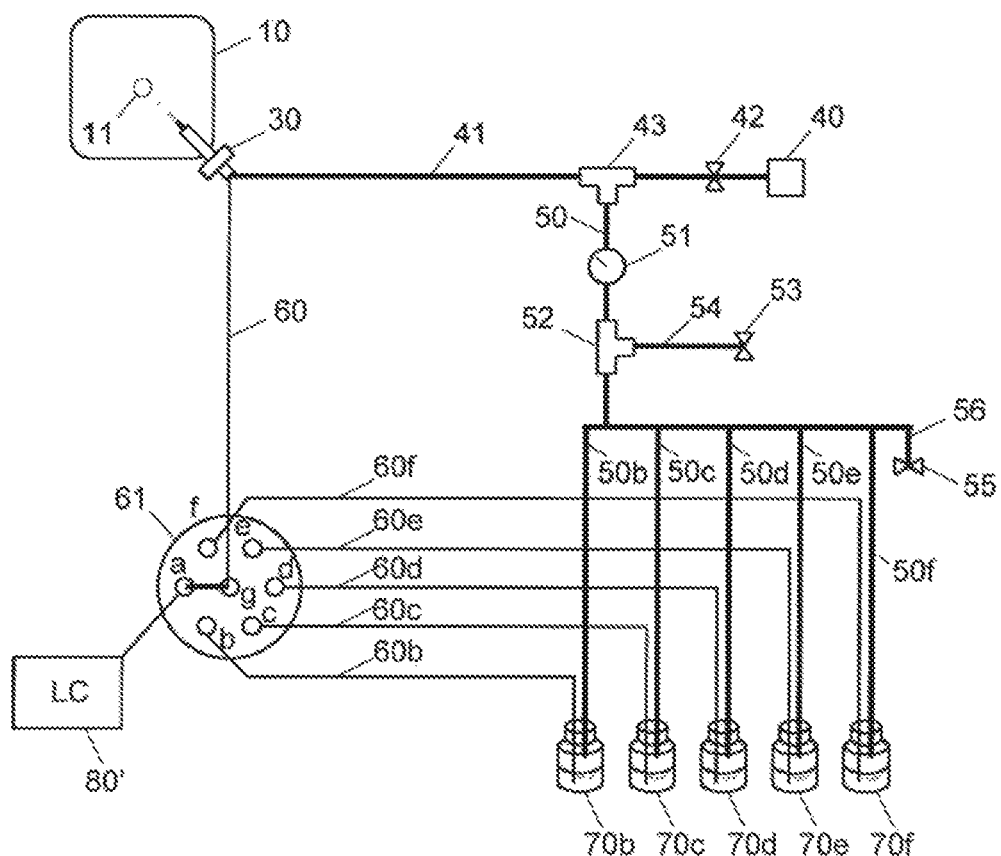
FIG. 3 is one example of the analysis conditions to be set in the present embodiment.
FIG. 4 is another configuration example of the liquid sample introduction system for an ion source according to the present invention.

A user enters analysis parameters for each of the one or more components which may possibly be contained in a target liquid sample, the parameters including: the name of the component; the time segment during which the component will be eluted from the column of the liquid chromatograph 80 (retention time); the mass range to be measured in a mass spectrometric analysis of the component in the TOF-MS; and the kind of reference liquid sample for mass calibration to be used as an internal reference in the mass spectrometric analysis of the component (or the identification number of the liquid sample container in which the reference liquid sample concerned is contained). Based on those parameters, the analysis condition setter 92 in the control unit 90 prepares an analysis condition file and saves it to the storage section 91. FIG. 3 shows one example of the analysis conditions. As for the reference liquid sample to be used in the mass spectrometric analysis of each component, a liquid sample should be selected which generates a plurality of kinds of ions which satisfy the condition that their mass-to-charge ratios are included within the mass range to be measured for the component and yet do not overlap the mass-to-charge ratios of the ions to be generated from the same component.

The present description deals with the case where the user enters the retention time, mass range to be measured, and kind of reference liquid sample for each component. As another possible case, component analysis information in which the information concerning the retention time, mass range to be measured and kind of reference liquid sample is related to each of the components may be stored in the storage section 91. In this case, upon receiving to an input of the name of a component by a user, the analysis condition setter 92 can refer to the component analysis information stored in the storage section 91 to automatically determine the retention time, mass range to be measured, and kind of reference liquid sample, and prepare an analysis condition file.

When a command to initiate an analysis is issued by the user, the analysis executer 93 introduces a target liquid sample into the liquid chromatograph 80. The target liquid sample is carried into the column by the flow of a mobile phase. After being temporally separated from each other within the column of the liquid chromatograph 80, the components in the target liquid sample (components A, B and C) are sequentially introduced into and ionized by the ESI probe 20, to be subjected to mass spectrometry.

Concurrently with the analysis operation, the liquid sample introduction system for an ion source sequentially supplies liquid samples to the ESI probe 30 as follows, based on the previously mentioned analysis conditions: The liquid sample in the liquid sample container 70*a* is supplied from the start of the measurement until the elapse of 4.5 minutes (until the middle point of the period of time between the ending time of the analysis of component A and the beginning time of the analysis of component B); the liquid sample in the liquid sample container 70*b* is supplied until the elapse of 7.0 minutes (until the middle point of the period of time between the ending time of the analysis of component B and the beginning time of the analysis of component C); and the reference liquid sample in the liquid sample container 70*d* is thereafter supplied to the completion of the analysis. When these liquid samples are supplied, the respective sections of the liquid sample introduction system for an ion source operate as described below.

Nitrogen gas is supplied from the nitrogen gas cylinder 40 into the nebulizer gas passage 41 at a flow rate of 3 L/min and with a pressure of +500 kPa, where L is the length of the passage from the ESI probe 30 to the valve 42. The notation of "+500 kPa" means that the pressure concerned is higher than the pressure in the ionization chamber 10 by 500 kPa. For example, if the ionization chamber 10 is at atmospheric pressure (101.325 kPa), the nitrogen gas is supplied with a pressure of 601.325 kPa. It should be noted that the numerical values of the flow rate and of the nitrogen gas supplied into the nebulizer gas passage 41 as well as the pressure of the liquid-supply gas are mere examples. The user may appropriately change those values. The flow rate and pressure of the nebulizer gas can be determined according to the specifications of the used ionization probe (in the present embodiment, ESI probe 30) and other relevant factors. The pressure of the liquid-supply gas can be determined according to the desired amount of reference liquid sample to be supplied. It should be noted that both the pressure of the nebulizer gas and that of the liquid-supply gas should be higher than the pressure within the ionization chamber 10.

The nitrogen gas flowing from the branching unit 43 into the liquid-supply-gas passage 50 is sent through the liquid-supply-gas sub-passages 50*a*-50*f* to the liquid sample containers 70*a*-70*f* after its pressure is reduced to +100 kPa by the regulator 51. Thus, the pressures in all liquid sample containers 70*a*-70*f* are simultaneously increased, whereby the reference liquid samples respectively contained in the liquid sample containers 70*a*-70*f* are pushed into the sample-supply sub-passages 60*a*-60*f*, respectively. If the gas pressure in the liquid-supply-gas passage 50 has increased to a level of +150 kPa or higher due to a problem with the regulator 51, the relief valve 53 is opened to release the nitrogen gas.

The reference liquid samples are supplied to the sample-supply sub-passages 60*a*-60*f* individually and to each the six sub-ports 61*a*-61*f* of the six-position seven-way valve 61. In the six position seven-way valve 61, only one of the sub-ports 61*a*-61*f* is connected to the main port 61*g*. Upon the initiation of the measurement, the reference liquid sample supplied to the sub-port 61*a* (the reference liquid sample contained in the liquid sample container 70*a*) passes through the main port 61*g* and flows into the sample-supply passage 60, and then is introduced into the ESI probe 30. Thereafter, the passage in the six-position seven-way valve 61 is switched according to lapse of analysis time, allowing the reference liquid samples b and d to be sequentially supplied to the ESI probe 30. When the analysis of the liquid sample is completed, and thus the supply of the liquid is discontinued, the valve 42 in the nebulizer gas passage 41 is closed, and then the atmospheric open valve 55 is opened to restore the liquid sample containers 70*a*-70*f* to ordinary pressure. Then, operations such as removal and exchange of the liquid sample containers 70*a*-70*f* are performed.

As described to this point, the liquid sample introduction system for an ion source according to the present invention has the liquid-supply-gas passage 50 connected to a point in the nebulizer gas passage 41 connected to the ESI probe 30. A portion of the nebulizer gas is thereby introduced into the liquid sample containers 70*a*-70*f*, and the reference liquid samples in the liquid sample containers 70*a*-70*f* are sent to the ESI probe 30 by the pressure of this nebulizer gas. Therefore, unlike the conventional system, it is unnecessary to provide a supply source of the liquid-supply gas for sending a liquid sample to the ESI probe, and the ionization of the liquid sample can be achieved at a low cost.

In a TOF-MS, if the temperature of the device or its surroundings changes, or if the voltage applied to a specific section in the mass spectrometer varies, the relationship between the mass-to-charge ratio and time of flight of the ion will also change. Since an analysis with a TOF-MS needs to achieve a high mass accuracy on the order of ppm, it is common to introduce a reference liquid sample as the internal reference for mass calibration during the mass spectrometric analysis of a target liquid sample. With the liquid sample introduction system for an ion source according to the present embodiment, the operation of changing the kind of reference liquid sample can be performed while maintaining the continuous supply of the nebulizer gas to the ESI probe 30. Accordingly, no fluctuation in the pressure or gas flow within the ionization chamber 10 occurs, and the components eluted from the liquid chromatograph 80 can be ionized under stable conditions.

The liquid sample introduction system for an ion source according to the present embodiment uses nebulizer gas for the supply of liquid samples. Nebulizer gas is generally used for atmospheric pressure ionization of liquid samples, regardless of the kinds of liquid samples. Therefore, the present system can be used for a wide variety of liquid samples and ionization methods.

The liquid sample introduction system for an ion source according to the present embodiment uses a single six-position seven-way valve 61 to select one of the six liquid samples to be introduced into the ESI probe 30. Therefore, it is unnecessary to provide a number of passage-switching units as in a conventional liquid sample introduction system for an ion source (e.g. the one described in Patent Literature 1). This reduces the risk of the sample contamination at a passage-switching unit.

A six-position seven-way valve may be provided at a position where the liquid-supply-gas passage 50 is branched into the six liquid-supply-gas sub-passages 50*a*-50*f*, thereby selectively increasing the pressure of the liquid sample containers 70*a*-70*f* to send the reference liquid sample. In this case, however, the pressure inside the liquid sample container containing a reference liquid sample that is not intended to be supplied is not increased. With the above configuration, the dead time upon switching the reference liquid samples to be supplied (a time period taken by the reference liquid sample to actually arrive at the ion source from the switching of the reference liquid samples) becomes longer. Accordingly, it is preferable to adopt the previously described configuration in which the single six-position seven-way valve 61 is disposed at the position where the sample-supply sub-passages 60*a*-60*f* and the sample-supply passage 60 are connected. This configuration shortens the dead time upon switching the reference liquid samples to be supplied.

Additionally, in the liquid sample introduction system for an ion source according to the present embodiment, the regulator 51 located in the liquid-supply-gas passage 50 allows the pressure of the liquid-supply gas to be regulated independently of the pressure of the nebulizer gas so as to appropriately change the amount of liquid sample to be supplied.

The previous embodiment is a mere example and can be appropriately changed within the spirit of the present invention.

In the previous embodiment, six kinds of reference liquid samples are selectively introduced into the ESI probe. The liquids to be supplied to the ESI probe 30 are not limited to reference liquid samples for mass calibration. For example, target liquid samples may also be introduced. A liquid for cleaning the sample supply passage 60 as well as the sample-supply sub-passages 60a-60f may also be supplied. As another example, as shown in FIG. 4, the sub-port 61a may be connected to the exit port of the liquid chromatograph 80' so as to introduce a target liquid sample (or the various components in the same sample) from the liquid chromatograph 80' into the ESI probe through the six-position seven-way valve 61 and the sample supply passage 60. In this case, it is unnecessary to provide the ESI probe 20 for introducing a target liquid sample.

In place of the six-position seven-way valve 61 used as the passage-switching unit in the previous embodiment, a passage-switching unit having an appropriate number of sub-ports may be used according to the number of liquid samples to be supplied.

Additionally, an APCI probe or other types of ionization probes may be used in place of the ESI probe 30 used as the ionization probe in the previous embodiment. In the case where an APCI probe is used, a drying gas can be used in place of the nebulizer gas in the previous embodiment. The drying gas is made to blow at the liquid sample from an opposite position to the tip of the APCI probe within the ionization chamber 10.

Although the passage-switching unit in the above embodiment is disposed between the sample-supply passage 60 and the sample-supply sub-passages 60a-60f, it is also possible to dispose the passage-switching unit between the liquid-supply-gas passage 50 and the liquid-supply-gas sub-passages 50a-50f, so as to selectively supply the liquid-supply gas to one of the liquid-supply-gas sub-passages 50a-50f.

REFERENCE SIGNS LIST

10 . . . Ionization Chamber
11 . . . Capillary
20, 30 . . . ESI Probe
40 . . . Nebulizer Gas Passage
40 . . . Nitrogen Gas Cylinder (Atomization Gas Source)
41 . . . Nebulizer Gas Passage
42 . . . Valve
43, 52 . . . Branching Unit
50 . . . Liquid-Supply-Gas Passage
50a-50f . . . Liquid-Supply-Gas Sub-Passage
51 . . . Regulator
52 . . . Branching Unit
53 . . . Relief Valve
54 . . . Relief Passage
55 . . . Atmospheric Open Valve
56 . . . Atmospheric Open Passage
60 . . . Sample-Supply Passage
60a-60f . . . Sample-Supply Sub-Passage
61 . . . Six-Position Seven-Way Valve
61a-61f . . . Sub-Port
61g . . . Main Port
70a-70f . . . Liquid Sample Container
80, 80' . . . Liquid Chromatograph
90 . . . Control Unit
91 . . . Storage Section
92 . . . Analysis Condition Setter
93 . . . Analysis Executer
94 . . . Input Unit
95 . . . Display Unit

The invention claimed is:

1. A liquid sample introduction system for an ion source comprising:
a first ionization probe into which a liquid sample to be analyzed is introduced;
a second ionization probe into which one of a plurality of reference liquid samples is selectively introduced;
a plurality of liquid sample containers, each of which is a hermetically closable container for holding a liquid sample;
a nebulizer passage configured to supply an atomization-promoting gas to the second ionization probe, and having one end connected to the second ionization probe;
a liquid-supply-gas passage having one end connected to the nebulizer passage, and another end connected to a space above a liquid level in one of the liquid sample containers; and
a sample supply passage having one end connected to a space below the liquid level in one of the liquid sample containers and another end connected to the second ionization probe,
wherein:
the other end of the liquid-supply-gas passage is branched into a plurality of liquid-supply-gas sub-passages each of which is connected to the space above the liquid level in one of the liquid sample containers;
the one end of the sample supply passage is branched into a plurality of sample-supply sub-passages each of which is connected to the space below the liquid level in one of the liquid sample containers;
and the liquid sample introduction system further includes:
a passage-switching unit, located at a branching point of the liquid-supply-gas passage, for selectively making one of the plurality of liquid-supply-gas sub-passages be in a communicating state, or a passage-switching unit, located at a branching point of the sample supply passage, for selectively making one of the plurality of sample-supply sub-passages be in a communicating state.

2. The liquid sample introduction system for an ion source according to claim 1, further comprising a liquid-supply-gas pressure regulator for regulating a pressure of the gas flowing through the liquid-supply-gas passage.

3. The liquid sample introduction system for an ion source according to claim 1, wherein the passage-switching unit is located at a branching point of the sample supply passage, for selectively making one of the sample-supply sub-passages be in a communicating state.

4. The liquid sample introduction system for an ion source according to claim 1, wherein the passage-switching unit is a passage-switching valve having one main port and a plurality of sub-ports to be selectively connected to the main port.

5. The liquid sample introduction system for an ion source according to claim 4, wherein one of the plurality of sub-ports is connected to an exit port of a liquid chromatograph.

6. An analyzing system, comprising:
   an ion analyzer for ionizing a target liquid sample after ionizing the liquid sample in an ionization chamber;
   the liquid sample introduction system for an ion source according to claim 1 for ionizing a reference liquid sample in the ionization chamber; and
   a processor configured to operate the liquid sample introduction system for an ion source so as to supply the reference liquid sample to the second ionization probe during an execution of an analysis of an ion generated from the target liquid sample.

7. The analyzing system according to claim 6, wherein the processor is further configured to operate the liquid sample introduction system to switch the passage-switching unit so as to supply a different kind of reference liquid sample to the second ionization probe according to a kind of ion generated from the target liquid sample.

8. The analyzing system according to claim 6, wherein the ion analyzer includes a time-of-flight mass separator section.

9. The analyzing system according to claim 7, wherein the ion analyzer includes a time-of-flight mass separator section.

* * * * *